(12) United States Patent
Cush et al.

(10) Patent No.: US 9,192,159 B2
(45) Date of Patent: Nov. 24, 2015

(54) AZOXYSTROBIN FORMULATIONS

(75) Inventors: Randall Cush, Greensboro, NC (US); Keith Parker, Singapore (SG); Joseph DiPaola, Greensboro, NC (US); David Ross, Greensboro, NC (US)

(73) Assignee: Syngenta Crop Protection, LLC, Greensboro, NC (US)

( * ) Notice: Subject to any disclaimer, the term of this patent is extended or adjusted under 35 U.S.C. 154(b) by 684 days.

(21) Appl. No.: 12/295,302

(22) PCT Filed: Mar. 28, 2007

(86) PCT No.: PCT/US2007/065313
§ 371 (c)(1),
(2), (4) Date: Mar. 18, 2009

(87) PCT Pub. No.: WO2007/118001
PCT Pub. Date: Oct. 18, 2007

(65) Prior Publication Data
US 2009/0222956 A1    Sep. 3, 2009

Related U.S. Application Data

(60) Provisional application No. 60/787,957, filed on Mar. 31, 2006.

(51) Int. Cl.
*A01N 43/54*     (2006.01)
*A01N 43/653*    (2006.01)
*A01N 25/02*     (2006.01)
*A01N 25/04*     (2006.01)

(52) U.S. Cl.
CPC .................................... *A01N 43/54* (2013.01)

(58) Field of Classification Search
CPC ........................................................ A01N 43/54
USPC ................. 424/484, 498, 502; 504/117, 363; 514/274, 397
See application file for complete search history.

(56) References Cited

U.S. PATENT DOCUMENTS

| | | |
|---|---|---|
| 5,242,907 A | 9/1993 | Dawson |
| 5,955,094 A | 9/1999 | Beall et al. |
| 6,683,211 B1 | 1/2004 | Lamberth et al. |
| 6,706,855 B1 | 3/2004 | Collins et al. |
| 2003/0118810 A1 | 6/2003 | Grantham et al. |
| 2005/0043182 A1* | 2/2005 | Douglass et al. ............. 504/363 |
| 2006/0171979 A1* | 8/2006 | Calvo et al. .................... 424/405 |
| 2009/0305889 A1* | 12/2009 | Cush ............................ 504/101 |

OTHER PUBLICATIONS

Bartlett et al., Review—The strobilurin fungicides; 2002; Pest Management Science, 58:649-662.*

* cited by examiner

*Primary Examiner* — Jane C Osowecki
(74) *Attorney, Agent, or Firm* — R. Kody Jones

(57) ABSTRACT

The present invention provides microemulsifiable concentrates and microemulsions comprising azoxystrobin and propiconazole.

16 Claims, No Drawings

AZOXYSTROBIN FORMULATIONS

This application is a National Stage Entry under 35 USC §371 of International application serial number PCT/US2007/065313, filed on Mar. 28, 2007, which claims priority to U.S. 60/787,957, filed on Mar. 31, 2006, the contents of which are incorporated herein by reference.

The present invention relates to liquid agrochemical compositions for application of an agriculturally active chemical to a plant, a pest or to a locus thereof. In particular, this invention relates to liquid compositions of agriculturally active chemicals that are in the form of microemulsions or microemulsifiable concentrates, the preparation of such compositions and a method of using such compositions to combat pests.

More particularly, the present invention relates to liquid formulations of azoxystrobin and propiconazole and the use thereof for disease control.

BACKGROUND OF THE INVENTION

When agriculturally active chemicals (agrochemicals) are relatively water soluble, preparing, storing, and shipping the same in a commercially acceptable form can be relatively clear-cut. However, many agrochemicals are hydrophobic and formulators are often confronted with difficulties in finding a suitable means for preparing these materials in stable formulations that deliver maximum loading of active ingredient per unit volume to the end-user.

A straight-forward approach to preparing concentrated liquid formulations with agrochemicals having limited aqueous solubility has been through the use of aromatic organic solvent systems. In such systems, aromatic organic solvents such as xylene or kerosene are used to solubilize the agrochemical compound of interest.

Commonly, surfactants are added to the agrochemical-solvent compositions to form emulsifiable concentrates. The surfactant-emulsifiers interact with the agrochemicals in a number of ways both before and during actual use, i.e., application to the site. The surfactants can initially disperse and/or emulsify the agrochemical in the solvent or in an inert carrier media and, for example, with herbicides, the surfactant composition may also act as a penetrant, spreader, sticker, stabilizer, and wetting agent. The surfactant composition may affect the rate of drying of a droplet on a plant and the nature of a residue liquid, or crystal. The surfactants may also influence the weathering characteristics of an agrochemical, including its rewetting characteristics and rainfastness.

Microemulsions are a subclass of emulsions and are typically clear solutions. In general, microemulsions are characterized by emulsion droplets having average particle sizes between 0.01 and 0.1 micron. The small particle size allows for the emulsion to be more stable than an emulsifiable concentrate formulation.

There is a need for microemulsifiable agrochemical concentrates that have a high biological activity in the target application, have good chemical and physical stability under a severe range of conditions that can be experienced in the marketplace, have good ecological and toxicological properties and can be readily water-dilutable to form a microemulsion.

Azoxystrobin, a strobilurin, is a fungicidal compound with a broad spectrum of disease control. Azoxystrobin inhibits mitochondrial respiration by blocking electron transfer between cytochrome b and cytochrome $c_1$, at the ubiquinol oxidising site. Azoxystrobin is a fungicide with protectant, curative, eradicant, translaminar and systemic properties and inhibits spore germination and mycelial growth, and also shows antisporulant activity. At labelled application rates, azoxystrobin controls the numerous pathogens including *Erysiphe graminis, Puccinia* spp., *Lepiosphaeria nodorum, Septoria tritici* and *Pyrenophora teres* on temperate cereals; *Pyricularia oryzae* and *Rhizoctonia solani* on rice; *Plasmopara viticola* and *Uncinula necator* on vines; *Sphaerotheca fuliginea* and *Pseudoperonospora cubensis* on cucurbitaceae; *Phytophthora infestans* and *Alternaria solani* on potato and tomato; *Mycosphaerella arachidis, Rhizoctonia solani* and *Sclerotium rolfsii* on peanut; *Monilinia* spp, and *Cladosporium carpophilum* on peach; *Pythium* spp. and *Rhizoctonia solani* on turf; *Mycosphaerella* spp. on banana; *Cladosporium caryigenum* on pecan; *Elsinoë fawcetii, Colletotrichum* spp. and *Guignardia citricarpa* on citrus; *Colletotrichum* spp. and *Hemileia vastatrix* on coffee. Azoxystrobin is a solid material having low solubility in water.

Propiconazole is a steroid demethylation (ergosterol biosynthesis) inhibitor. Propiconazole is a systemic foliar fungicide with protective and curative action, with translocation acropetally in the xylem. At labelled application rates, propiconazole controls numerous diseases caused by, for example, *Cochliobolus sativus, Erysiphe graminis, Leptosphaeria nodorum, Puccinia* spp., *Pyrenophora teres, Pyrenophora tritici-repentis, Rhynchosporium secalis* and *Septoria* spp. on cereals; *Mycosphaerella musicola* and *Mycosphaerella fijienis* var. *difformis* in bananas; *Sclerotinia homoeocarpa, Rhizoctonia solani, Puccinia* spp., *Erysiphe graminis* in turf; *Rhizoctonia solani, Helminthosporium oryzae* and dirty panicle complex in rice; *Hemileia vastatrix* in coffee; *Cercospora* spp. in peanuts; *Monilinia* spp., *Podosphaera* spp., *Sphaerotheca* spp. and *Tranzschelia* spp. in stone fruit; and *Helminthosporium* spp in maize. Propiconazole is a substantially water-insoluble liquid at 20° C.

Water-dispersible granular formulations of azoxystrobin are currently known for use on turf grass, Microemulsifiable concentrates of azoxystrobin have been prepared and are commercially available under the name of, for example, HERITAGE® TL fungicide available from Syngenta Crop Protection, Inc. (Greensboro, N.C., USA). HERITAGE® TL fungicide is a liquid formulation having many properties characteristic of a microemulsifiable concentrate. Upon dilution, while not truly thermodynamically stable, HERITAGE® TL forms an optically transparent emulsion having average emulsion droplet sizes in the range of 0.01 to 0.1 microns and is stable for extended periods of time, Microemulsifiable concentrates of other fungicides are known as well including microemulsifiable concentrates of propiconazole commercially available under the name of, for example. Banner MAXX® fungicide available from Syngenta Crop Protection, Inc. (Greensboro, N.C., USA). As described above, the microemulsifiable concentrates do provide a number of advantages upon dilution, for example, they mix very easily with water and require minimal agitation. The microemulsions formed are quite stable, the emulsion droplet average particle size is smaller than that of an emulsifiable concentrate and biological activity may be superior.

It is often desirable to use mixtures of fungicides having different modes of action in order to increase the spectrum of fungal disease control as well as a means for resistance management. Mixtures of azoxystrobin and propiconazole are known and include QUILT™ fungicide, a suspoemulsion formulation commercially available from Syngenta Crop Protection, Inc. (Greensboro, N.C., USA). In this suspoemulsion, the azoxystrobin is present as a dispersed solid, while the propiconazole is in a dispersed liquid state.

While microemulsions prepared by diluting microemulsifiable concentrates are relatively stable compared to other formulation types, when the active ingredient starting materials are high melting solids, there is the possibility that these materials can crystallize and fall out of solution over time. This has been observed in microemulsions of azoxystrobin. When initially formed the formulations have an average emulsion droplet size of between 0.01 and 0.1 microns, however, over time the azoxystrobin can re-crystallize and settle. It is one object of the present invention to prepare microemulsifiable concentrates which, upon dilution, form liquid azoxystrobin microemulsion formulations having prolonged physical stability.

SUMMARY OF THE INVENTION

It has been found that when microemulsifiable concentrates comprising azoxystrobin and propiconazole are diluted in a sufficient amount of water to form a microemulsion, the microemulsions exhibit enhanced physical stability compared to similarly formulated azoxystrobin emulsions which do not contain propiconazole; the novel compositions are storage stable, easy to apply, ecological and toxicologically favorable and, upon dilution with water, are useful as agrochemical compositions that have good biological efficacy in the target application and exhibit prolonged physical stability upon dilution in water.

DETAILED DESCRIPTION OF THE INVENTION

Accordingly, the present invention provides a microemulsifiable, storage stable, liquid, agrochemical concentrate comprising azoxystrobin, an effective amount of a solvent or solvent blend capable of dissolving or solubilizing the azoxystrobin, propiconazole and an effective amount of an emulsifier system capable of forming a microemulsion of azoxystrobin and propiconazole upon dilution in water. The relative proportion of said azoxystrobin, solvent(s), propiconazole and emulsifier system being such that upon dilution of said concentrate with adequate water, a stable oil-in-water microemulsion is spontaneously formed.

Substantially water-insoluble active chemical agents, such as propiconazole, that, are liquid at room temperatures can be dispersed with emulsifiers alone in water without the need for a solvent. In the event that the substantially water-insoluble pesticidally active ingredient is a high viscosity liquid or a solid, such as azoxystrobin, solvents may be used to dissolve or solubilize the substantially water-insoluble pesticidally active ingredient and form a low viscosity liquid.

It has been found that mixing azoxystrobin technical with propiconazole, surfactants and solvents, optionally with heating, for example to 40° C., to dissolve or solubilize the azoxystrobin technical results in a microemulsifiable concentrate which, upon dilution in a suitable amount of water to form a microemulsion, results in a formulation having prolonged physical stability compared, to similarly formulated azoxystrobin formulations which do not contain propiconazole. As used herein, the term "microemulsifiable concentrate" encompasses concentrates of active chemical agents which, upon dilution in water, form a microemulsion, defined herein as formulations having an average emulsion droplet size of between 0.01 and 0.1 micron, even if the emulsion formed upon dilution is not thermodynamically stable. Typically, the azoxystrobin will be present in the concentrate in an amount of from 0.1 to 25%, preferably 0.1 to 15%, by weight. Propiconazole will typically be present in the concentrate in an amount of from 0.1 to 25% by weight. Azoxystrobin and propiconazole are preferably present in the composition of the present invention in a ratio of from 10:1 to 1:10, preferably 5:1 to 1:5 and more preferably from 3:1 to 1:3.

Solvents for use in the present invention may be water-miscible or water-immiscible solvents, or combinations thereof. Selection of an appropriate solvent can readily be determined by one skilled in the art.

Water-immiscible solvents which may be used, include aliphatic and aromatic hydrocarbons such as hexane, cyclohexane, benzene, toluene, xylene, mineral oil or kerosene, mixtures or substituted naphthalenes, mixtures of mono- and polyalkylated aromatics commercially available under the registered trademarks SOLVESSO®, ISOPAR®, SHELLSOL®, PETROL SPEZIAL® and AROMATIC®, halogenated hydrocarbons such as methylene chloride, chloroform and o-dichlorobenzene; phthalates, such as dibutyl phthalate or dioctyl phthalate, ethers and esters, such as ethylene glycol monomethyl or monoethyl ether, fatty acid esters; lactones such as butyrolactone; ketones, such as cyclohexanone; higher alcohols such as hexanol and octanol; plant oils such as castor oil, soybean oil, cottonseed oil and possible methyl esters thereof; as well as epoxidised coconut oil or soybean oil. Preferred water-immiscible solvents are aliphatic and aromatic hydrocarbons, petroleum based esters, fatty acid esters (e.g. WITCONOL 2309), dipropyleneglycol monomethylether (e.g. DOWANOL DPM) and castor oil.

Suitable alkyl alkanoate ester solvents include the $C_6$-$C_{13}$ alkyl $C_{1-4}$ alkanoates such as the oxo-hexyl, oxo-heptyl, oxo-octyl, oxo-nonyl, oxo-decyl, oxo-dodecyl and oxo-tridecyl formates, acetates, propanoates, and butanoates; preferably the $C_6$-$C_{13}$ alkyl acetates. These materials are generally commercially available or can be readily made by those of ordinary skill in the art. A number of the foregoing alkyl acetates are commercially available. Particularly advantageous $C_6$-$C_{13}$ alkyl acetates are available from Exxon Mobil Corporation under the general trade designation "EXXATE".

Suitable polyhydric alcohols and polyhydric alcohol condensates include propylene glycol; dipropylene glycol; poly$C_{2-6}$alkylene glycols and derivatives preferably poly-($C_{2-6}$-alkylene) glycol and derivatives such as polypropylene glycol [M.W. 2000-4000], polyoxyethylene polyoxypropylene glycols, polyoxypropylene polyoxyethylene glycols, diethyleneglycol, polyethylene glycol [M.W. 200-4000 amu], methoxy polyethylene glycols 350, 550, 750, 2000, 5000; glycerol; ethoxylated glycerol; propoxylated glycerol; sugar alcohols and their alkoxylated derivatives such as xylitol, mannitol, sorbitol, ethoxylated sorbitol, hydroxy propyl sorbitol; hexylene glycol (2-methyl-2,4-pentanediol); 1,3-butylene glycol; 1,2,6-hexanetriol; ethohexadiol USP (2-ethyl-1,3-hexanediol); $C_{15}$-$C_{18}$vicinal glycol and polyoxypropylene derivatives of trimethylolpropane, short-chain up to 7 carbons, preferably up to 4 carbons aliphatic glycols, and glycerine.

Particularly suitable water-immiscible solvents include methyl esters of fatty acids derived from fats and oils such as methyl oleate, n-octanol, alkyl phosphates such as tri-n-butyl phosphate, alkylene carbonates such as propylene carbonate and isoparaffinic solvents.

Water-miscible solvents such as tetrahydrofurfuryl alcohol, ethyl lactate, gamma-butyrolactone, N-methyl-2-pyrrolidone, tetramethylurea, dimethyl sulfoxide, N,N-dimethylacetamid and dimethylformamide may be used alone or as co-solvents with the water-immiscible solvents described above.

Preferably, the solvent(s) is/are present in an amount of from about 30% to about 75% by weight of the microemulsifiable concentrate.

The selection of appropriate surfactant(s) for the emulsifier system can be made by one of skill in the art without undue experimentation. Typically, the amount of emulsifiers needed in a microemulsion is larger than that in an emulsion. The emulsifier system comprises at least one surfactant capable of forming a microemulsion of azoxystrobin and propiconazole upon dilution in water, for example, at least one non-ionic surfactant such as a condensation product of castor oil and a poly$C_{2-4}$alkylene oxide. Combinations of strongly hydrophobic (HLB>9, preferably >13) non-ionic surfactants and hydrophobic anionic surfactants are also preferred emulsifiers for forming microemulsions.

The term "surfactant" as used in the present specification means a chemical substance that acts as a surface active agent which can provide foaming, wetting, dispersing and emulsifying properties and which is cationic, anionic, nonionic or amphoteric.

As co-surfactants, nonionic surfactants with low HLB or short-chain ($C_4$ to $C_{10}$) alkyl alcohols may be used to lower the HLB of the formulation and to reduce surface tension between water and oil. Solvents, such as fatty acid methyl esters having a carbon chain length of 8 to 12 may provide desired solubility and emulsification characteristics.

Choosing an appropriate surfactant and co-surfactant, if necessary, and the other components of the microemulsifiable concentrate is possible to one of ordinary skill in the art without undue experimentation. A useful guide to preparing microemulsions can be found in U.S. Pat. No. 5,242,907, the contents of which are incorporated herein by reference. The amount of surfactants required to emulsify an oil will depend on the amount of oil in the emulsion, more specifically the interfacial surface area which is proportional to the amount of emulsified oil at a constant particle size.

In one embodiment, the emulsifier system can comprise a single surfactant, for example a non-ionic surfactant such as a condensation product of castor oil and a poly$C_{2-4}$alkylene oxide. In a preferred embodiment, the emulsifier system comprises a blend of surfactants comprising at least one anionic or cationic surfactant and at least one nonionic surfactant. Preferably, the emulsifier system comprises surfactant(s) in an amount of from about 5% to about 40% by weight of the microemulsifiable concentrate.

Examples of useful surfactants include nonionic surfactants selected from the group consisting of (1) a mono $C_{2-6}$alkyl ether of a poly$C_{2-4}$alkylene oxide block copolymer having at least a first polyalkylene oxide block region and a second polyalkylene oxide block region in which the polyalkylene oxide in said first region is different than the polyalkylene oxide in said second region. Preferably, the $C_{2-6}$alkyl ether portion is a $C_{3-5}$alkyl ether, more preferably a $C_4$alkyl ether, of the alkylene oxide block copolymer. Also preferably, the alkylene oxide block copolymer portion is preferably an ethylene oxide/propylene oxide block copolymer. Preferably the ethylene oxide portion represents from about 10 to about 90 mole % to from about 25 to about 75 mole % of the block copolymer. A particularly preferred material is available under the trade name Ethylan NS-500LQ, available from Akzo Nobel; (2) a condensation product of castor oil and a poly$C_{2-4}$alkylene oxide. Preferably the alkylene oxide portion is ethylene oxide. Preferably the degree of alkoxylation is from about 10 moles to about 100 moles of alkylene oxide per mole of castor oil, more preferably about 20 moles to about 70 moles of alkylene oxide per mole of castor oil. A highly preferred alkoxylated castor oil is available under the trade name Agnique CSO-36 from Cognis; (3) a mono- or di ester of a $C_{12-24}$fatty acid and poly$C_{2-4}$alkylene oxide, where the fatty acid groups may be the same or different. Preferably, the fatty acid groups are the same when two such groups are present. Also preferably, the fatty acid groups are $C_{12-20}$fatty acid groups, more preferably $C_{12-18}$fatty acid groups, most preferably lauroyl, oleic, caprylic or myristoleic. In addition, the poly$C_{2-4}$alkylene oxide portion is preferably polyethoxy and the number of alkylene oxide groups in the poly$C_{2-4}$alkylene oxide portion is preferably from about 2 to about 40 repeating units. Highly preferred materials of this type include Kessco PEG 400DL (Stepan) and Emerest 2620 (Cognis).

In a particular embodiment the formulation of the present invention comprises, as a non-ionic surfactant, a copolymer of propylene oxide (PO) and ethylene oxide (EO) and/or an ethoxylated tristyrene phenol. A suitable copolymer of PO and EO is alpha-butyl-omega-hydroxypoly (oxypropylene) block polymer with poly (oxyethylene) and has a molecular weight of 2400 to 3500. Commercially available examples of this copolymer are Toximul®, Witconol® and Atlas®. In a particular embodiment of the present invention, the copolymer is present in the microemulsifiable concentrate at between about 0.5 and about 10 weight % and preferably at about 1 to 5 weight %. A suitable ethoxylated tristyrene phenol is alpha-[2,4,6-tris[1-(phenyl)ethyl]phenyl]-omega-hydroxy poly(oxyethylene). Suitably, the poly(oxyethylene) content averages from about 4 to about 150 moles. A commercially available example of this surfactant is Soprophor BSU®. In a particular embodiment, this surfactant is present in the concentrate at between about 1 and about 15 weight % and preferably from 6 to 10 weight %.

Suitable anionic surfactants include a poly(oxy-1,2-ethanediyl)-alpha-$C_{10-15}$alkyl-omega-hydroxy phosphate or sulphate and/or a $C_{10-13}$alkylbenzenesulfonic acid. Preferably, the a poly(oxy-1,2-ethanediyl)-alpha-$C_{10-15}$alkyl-omega-hydroxy phosphate or sulphate is a poly(oxy-1,2-ethanediyl)-alpha-tridecyl-omega-hydroxy phosphate or sulphate. Also, the (oxy-1,2-ethanediyl) portion of the compound is present in about 3 to about 9, preferably about 6, repeating units per molecule. A suitable compound for the poly(oxy-1,2-ethanediyl)-alpha-$C_{10-15}$alkyl-omega-hydroxy phosphate is available as Stepfac 8181 (Stepan). A suitable compound for the $C_{10-13}$alkylbenzenesulfonic acid is Biosoft S-100 (Stepan). Additional suitable anionic surfactants include the phosphate and sulphate derivatives of ethoxylated alkyl phenols such as -[EO]$_{2-20}$-di and tristyrylphenols, nonylphenols, dinonylphenol and octylphenols.

Where salts of the phosphate or sulphate group are desirable, the salt may be a salt with any base so long as the base is not incompatible with any of the other ingredients including the agrochemical. Particularly suitable are the phosphate salts of alkali metals, alkaline earth metals, ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine.

In another embodiment, the anionic surfactant is a styrylphenol polyethoxy ester phosphate. A suitable anionic surfactant is alpha-[2,4,6-tris[1-(phenyl)ethyl]phenyl]-omega-hydroxy poly(oxyethylene) ester phosphate. In particular, this compound is present as a mixture of the mono-hydrogen and dihydrogen phosphate esters and the corresponding ammonium, calcium, magnesium, potassium, sodium and zinc salts. Suitably, the poly(oxyethylene) content averages from about 4 to about 150 moles. A commercially available example of this surfactant is Soprophor 3D33®. In a particular embodiment, this surfactant is present at between about 5 and about 1.0 weight % and preferably at about 8.5 weight %.

Cationic surfactants suitable for use in the present invention include polyC$_{2-4}$alkoxylated C$_{14-20}$fatty amines, preferably the polyC$_{2-4}$alkoxylated C$_{12-18}$fatty amines, most preferably a polyC$_{2-4}$alkoxylated tallow amine. The polyC$_{2-4}$alkoxylated portion of this component is preferably present in either 2-8 (more preferably 2-5) repeating units per molecule or the polyC$_{2-4}$alkoxylated portion of this component is preferably present in about 14 to about 18 (more preferably about 16) repeating units per molecule or more preferably is -[EO]$_{2-20}$-; and mixtures thereof. Particularly useful amine compounds include the Toximuls such as TA-2, -3, -4, -5, -6, -7, -7, -8, -9, -10, -11, -12, -13, -14, -15, -16, -17, -18, -19 and -20 (Stepan); and mixtures thereof. Additional suitable cationic surfactants include the fatty acid alkanol amides such as, for example, the Witcamides (Witco).

Another aspect of the invention is a process for preparing a liquid microemulsifiable agrochemical concentrate as herein described, by intimately mixing, optionally by warming, the azoxystrobin, propiconazole, solvent(s) and emulsifier system until a homogeneous phase is achieved.

In another aspect of the invention the microemulsifiable concentrate, on dilution with water, forms a microemulsion useful as a ready-to-use aqueous spray mixture. The microemulsions of the present invention are compositions having emulsion droplets having average particle sizes between 0.0.1 and 0.1 micron, optionally optically transparent, and which exhibit prolonged physical stability compared to microemulsions of azoxystrobin alone. For purposes of this invention, the term "optically transparent" is defined as compositions having no or almost no attenuation of transmitted light, preferably a complete lack of any visible nonuniformity when viewed in mass, in bottles or test tubes, by strong transmitted light. This includes microemulsions that may appear slightly hazy due to the presence of emulsion droplets having an emulsion droplet size at the upper size limits of the described ranges.

Microemulsions of any required dilution can be obtained from this concentrate by dilution with water and can be used, for example, in the protection and enhancement of the health, quality and productivity of useful plants and for the control of diseases (whether on agricultural, residential, commercial or public land). Using such dilutions it is possible to treat living plants and also plant propagation material by spraying, watering or impregnation. The microemulsions also are suitable for the protection and preservation of wood and other materials. For example, prior to the application, the microemulsifiable concentrate of the invention may be diluted with water by simple mixing at ambient temperature in order to get a ready for use spray mixture. Generally, the active ingredients are present in the spray mixture in a concentration of from about 0.001 to about 1% by weight. In one embodiment, the microemulsifiable concentrate is contacted with a first fraction of water to prepare a microemulsion concentrate thereof and said microemulsion concentrate is further diluted with an additional fraction of water to result in said final microemulsion whereby said final microemulsion may result before or during the act of dispensing said agrochemical.

One embodiment of the present invention is directed to a method of improving the physical stability of an azoxystrobin microemulsion, said method comprising forming a microemulsifiable concentrate comprising azoxystrobin, propiconazole, an emulsifier system and at least one solvent capable of dissolving or solubilizing azoxystrobin and diluting said microemulsifiable concentrate with an appropriate amount of water to form a microemulsion, wherein said microemulsion exhibits improved physical stability compared to a similarly formulated azoxystrobin microemulsion which does not contain propiconazole.

Another embodiment is directed to a method of improving the physical stability of an azoxystrobin microemulsion, said method comprising forming a microemulsifiable concentrate comprising azoxystrobin, at least one solvent suitable for dissolving or solubilizing azoxystrobin and an emulsifier system suitable for forming an emulsion of azoxystrobin having an average emulsion particle size of between 0.01 and 0.1 micron upon dilution in water, and diluting said microemulsifiable concentrate to form a microemulsion, wherein propiconazole is mixed with the azoxystrobin prior to, during and/or after dilution of the azoxystrobin-containing microemulsifiable concentrate.

The present invention also provides for use of the formulation of the invention to control fungal disease in turfgrass and methods of controlling fungal disease by applying the formulation of the invention to turfgrass. In particular, the formulation of the present invention may be used for control of pathogens causing foliar, stem and root diseases of turfgrass plants. These diseases include, but are not limited to leaf and stem blights, leaf spots, patch diseases, mildews, anthracnose, fairy rings, molds and rusts. In particular, the formulation of the present invention may be used to control *Colletotrichum graminicola* (Anthracnose), *Rhizoctonia solani* (Brown Patch, *Rhizoctonia* Large Patch), *Rhizoctonia cerearalis* (Cool Weather Brown Patch, Yellow Patch), *Lycoperdon* spp., *Agrocybe pediades* and *Bovistra plumbea* (all of which cause Fairy Rings), *Microdocium nivale* (Fusarium Patch, Pink Snow Mold), *Pyricularia grisea* (Gray Leaf Spot), *Typhula incarnata* (Gray Snow Mold, *Typhula* Blight), *Puccinia* spp, (Leaf Rust, Stem Rust, Stripe Rust), *Bipolis sorokiniana* (Leaf Spot), *Drechslera poae* (Melting Out), *Leptosphaeria korrae* (Necrotic Ring Spot), *Limonomyses roseipellis* (Pink Patch), *Erysiphe graminis* (Powdery Mildew), *Pythium aphanidermatum* and other *Pythium* species (*Pythium* Blight, *Pythium* Root Rot), *Laetisaria fuciformis* (Red Thread), *Rhizoctania zeae* (*Rhizoctania* Leaf Spot), *Sclerotium rolfsii* (Southern Blight), *Lepiosphaeria korrae*, *Gaeumannomyces graminis* var. *graminis* or *Ophiosphaerella herpotricha* (all of which cause Spring Dead Spot), *Magnaporthe poae* (Summar Patch), *Gaeumannomyces graminis* var. *avenae* (Take-all Patch), *Rhizoctonia solani* and *Gaeumannomyces incrustana* (both of which may cause Zoysia Patch) and *Sclerotinia homeocarpa* (Dollar Spot).

The term "turfgrass" includes, but is not limited to, turfgrass on golf course, lawns and landscape areas around residential, institutional, public, commercial and industrial buildings, parks, recreational areas and athletic fields.

In addition, it is noted mat the formulation of the present invention may also be used to control fungal disease on ornamental plants such as woody plants and perennials.

The formulation as described herein may be applied using conventional techniques. In particular, the formulations may be applied as a foliar spray, perhaps in alternating spray programs, or in tank; mixes with, for example, other turf protection products such as fungicides, fertilizers, herbicides, insecticides and biological control products. When applied as a foliar spray, the formulations as described herein may conveniently be applied with spray equipment commonly used for making ground applications. In addition, the formulations may also be applied using a liquid fungicide injector to allow control of ectrotrophic root diseases (for example. Summer Patch and Take-all Patch).

Suitably, the formulation of the present invention is applied prior to disease development. Rates of use of the formulation are those conventionally used in the art. Suitably, 0.1 to 5.5 fluid ounces of the formulation are used per 1000 square feet of turf grass to be treated, depending on the disease targeted. Most suitably, 1 to 2 fluid ounces of formulation per 1000 square feet is used. The formulation of the invention may be applied in a single application or repeatedly at an interval of, suitably, between 1.0 and 28 days.

Microemulsions of the invention are easily prepared by well known methods and using standard equipment in the art. A beaker or laboratory pot is adequate for low volume purposes, while larger volumes may be processed in standard industrial agitated tankage including reactors, dissolves and bulk tanks. Agitation requirements are not critical and agitation need only be adequate to provide a homogeneous formulation. Medium speed agitation with stir bars, or agitators fitted with standard industrial props are preferred. Baffled tanks are preferred in industrial applications as a means to reduce vortexing and air entrainment, and to minimize the agitator prop speed required to achieve desired homogeneity. Heated or jacket vessels are preferred. High shear and high speed mixing are not preferred if excessive air entrapment in the formulation can occur. The composition constituents may be added in any order into a suitable vessel. Preferably, the surfactants and solvents are first added followed by the pesticidally active ingredients. Surfactants that are not flowable at the processing temperature may optionally be melted prior to formulation, or preferably melted in the processing equipment before the balance of the components are added.

Suitably, the solvent is added to a reactor vessel and heated and agitated while the surfactants are added. Finally, the pesticidally active ingredients, azoxystrobin and propiconazole, are added and the solution maintained at a specific temperature (suitably at less than 45° C.) and mixed until the azoxystrobin is completely dissolved or solubilized.

The invention will now be described with reference to the following, non-limiting examples:

EXAMPLES

The solvent and surfactants described below were added to a reactor vessel with the capacity to heat and were agitated. Finely milled azoxystrobin technical and propiconazole technical, when present, were added. When necessary to dissolve the azoxystrobin technical the concentrates were heated to around 40° C. until the azoxystrobin technical was dissolved.

The following tests were run to compare the dilution properties of a concentrate containing azoxystrobin alone (Comparative Example 1) to concentrates comprising both azoxystrobin and propiconazole (Examples 1 to 6), 96 mL of 342 ppm hardness water was added to 100 mL cylinders. Four (4) mL of the concentrates of Examples 2 to 6 were added to the cylinders. The amount of concentrate from Example 1 and Comparative Example 1 were added to the cylinders in an amount sufficient to yield the same concentration of azoxystrobin upon dilution (4.57 mL and 3 mL, respectively). The cylinders were capped and inverted 15 times to mix thoroughly. The cylinders were allowed to sit without agitation at room temperature and checked periodically for sediment of crystallized active ingredient.

The final amounts (wt. %) of concentrate components are set forth in Table 1.

TABLE 1

| Ingredient | Function | Example 1 | Example 2 | Example 3 | Example 4 | Example 5 | Example 6 | Comparitive Example 1 |
|---|---|---|---|---|---|---|---|---|
| Tetrohydrofurfuryl alcohol | Solvent | 70.91 | 64.19 | 69.19 | 35.59 | 36.59 | 75.19 | 70.93 |
| Ethyl lactate | Solvent | 0 | 0 | 0 | 35.60 | 36.60 | 0 | |
| Butyl ether derivative of EO/PO block copolymer (Toximul ® 8320 available from Stepan) | Non-ionic surfactant | 0 | 3.00 | 0 | 0 | 0 | 0 | 3.0 |
| Tristyrylphenol ethoxylate with approximately 16 moles ethoxylation (Soprophor ® BSU available from Rhodia) | Non-ionic surfactant | 11.10 | 8.50 | 0 | 11.00 | 11.00 | 9.00 | 8.5 |
| Polyethylene glycol dilaurate (PEG 400DL available from Stepan) | Non-ionic surfactant | 2.02 | 0 | 0 | 2.00 | 0 | 0 | |
| Tristyrylphenol ethoxylate phosphate ester (Soprophor ® 3D33 available from Rhodia) | Anionic surfactant | 0 | 8.50 | 15.00 | 0 | 0 | 0 | 8.5 |
| Azoxystrobin technical (purity 97%) | Active ingredient | 5.92 | 5.86 | 5.86 | 5.86 | 5.86 | 5.86 | 9.07 |
| Propiconazole technical (purity 95%) | Active ingredient | 10.05 | 9.95 | 9.95 | 9.95 | 9.95 | 9.95 | 0 |
| Observations: Time till crystallization or sedimentation | | Trace sediment visible after 70 hours | 3.5 days | 4 days | 3 days | 4 days | 4 days | Sediment clearly visible after 24 hours |

From the results in the above Table, it is clear that concentrates containing both azoxystrobin and propiconazole (Examples 1 to 6) exhibit prolonged physical stability upon dilution in water compared to a similarly formulated azoxystrobin composition which did not contain propiconazole.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A microemulsifiable concentrate consisting essentially of:
   a) azoxystrobin;
   b) propiconazole;
   c) an emulsifier system capable of forming a microemulsion of azoxystrobin and propiconazole upon dilution in water, wherein said emulsifier system comprise surfactant(s) in an amount of from about 5% to about 40% by weight of the microemulsifiable concentrate; and d) at least one water-miscible solvent capable of dissolving or solubilising azoxystrobin, wherein said water-miscible solvent(s) is/are present in an amount of from about 60% to 75% by weight of the microemulsifable concentrate;

wherein said azoxystrobin and said propiconazole are present in a ratio of from 10:1 to 1:10; and wherein, when 4 mL of the microemulsifiable concentrate is diluted in 96 mL of water, the resultant microemulsion is optically transparent in appearance after 24 hours at 25° C.; and e) at least one non-ionic surfactant, or a mixture of at least one non-ionic surfactant and at least one anionic surfactant.

2. The microemulsifiable concentrate of claim 1 wherein the emulsifier system comprises a condensation product of castor oil and a $polyC_{2-4}$alkylene oxide.

3. The microemulsifiable concentrate of claim 1 wherein the solvent comprises tetrahydrofurfuryl alcohol.

4. The microemulsifiable concentrate of claim 1 wherein said azoxystrobin is present in an amount of from about 0.1% to about 25% by weight of the microemulsifiable concentrate.

5. The microemulsifiable concentrate of claim 1 wherein said propiconazole is present in an amount of from about 0.1% to about 25% by weight of the microemulsifiable concentrate.

6. A stable oil-in-water microemulsion comprising the microemulsifiable concentrate of claim 1 and water, wherein the oil-in-water microemulsion is optically transparent in appearance at 25° C.

7. A stable oil-in-water microemulsion comprising the microemulsifiable concentrate of claim 1 and water which has emulsion droplets with an average particle size of between 0.01 and 0.1 micron.

8. A microemulsion comprising a microemulsifiable concentrate of claim 1 and water.

9. The microemulsion of claim 6 in the form of a sprayable composition.

10. A method of dispensing hydrophobic agrochemicals comprising diluting said microemulsifiable concentrate of claim 1 with water to form an aqueous microemulsion thereof, and dispensing said aqueous microemulsion.

11. A method of treating a plant with an agrochemical composition comprising diluting said microemulsifiable concentrate of claim 1 with water to form a microemulsion, and exposing said plant or portion of said plant to said microemulsion.

12. A method of treating soil with an agrochemical composition in preparation for planting comprising diluting said microemulsifiable concentrate of claim 1 with water to form a microemulsion, and exposing said soil to said microemulsion.

13. A method of treating seed with an agrochemical composition comprising diluting said microemulsifiable concentrate of claim 1 with water to form a microemulsion, and exposing said seed to said microemulsion.

14. A plant or plant part treated with a microemulsion of an agrochemical composition, said microemulsion being an aqueous dilution of a microemulsifiable concentrate of claim 1.

15. A method of improving the physical stability of an azoxystrobin microemulsion, said method comprising forming a microemulsifiable concentrate consisting essentially of azoxystrobin, propiconazole, an emulsifier system and at least one solvent capable of dissolving or solubilising azoxystrobin and diluting said microemulsifiable concentrate with water to form a microemulsion, wherein said microemulsion exhibits improved physical stability compared to a similarly formulated azoxystrobin microemulsion which does not contain propiconazole.

16. A method of improving the physical stability of an azoxystrobin microemulsion, said method comprising forming a microemulsifiable concentrate consisting essentially of azoxystrobin, at least one solvent suitable for dissolving or solubilising azoxystrobin and an emulsifier system suitable for forming an emulsion of azoxystrobin having an average emulsion particle size of between 0.01 and 0.1 micron upon dilution in water, and diluting said microemulsifiable concentrate to form a microemulsion, wherein propiconazole is mixed with the azoxystrobin prior to, during and/or after dilution of the azoxystrobin-containing microemulsifiable concentrate.

* * * * *